United States Patent
Hall et al.

(10) Patent No.: US 6,740,103 B2
(45) Date of Patent: May 25, 2004

(54) MAGNETICALLY NAVIGABLE AND/OR CONTROLLABLE DEVICE FOR REMOVING MATERIAL FROM BODY LUMENS AND CAVITIES

(75) Inventors: Andrew F. Hall, St. Charles, MO (US); Jeffrey Garibaldi, St. Louis, MO (US); Peter R. Werp, St. Louis, MO (US); John M. Lasala, St. Louis, MO (US)

(73) Assignee: Stereotaxis, Inc., St. Louis, MO (US)

(*) Notice: Subject to any disclaimer, the term of this patent is extended or adjusted under 35 U.S.C. 154(b) by 0 days.

(21) Appl. No.: 10/212,458

(22) Filed: Aug. 5, 2002

(65) Prior Publication Data

US 2003/0014066 A1 Jan. 16, 2003

Related U.S. Application Data

(63) Continuation of application No. 09/281,241, filed on Mar. 30, 1999, now Pat. No. 6,428,551, which is a continuation-in-part of application No. 09/165,694, filed on Oct. 2, 1998, now abandoned.

(51) Int. Cl.[7] .............................................. A61B 17/32
(52) U.S. Cl. ...................................................... 606/167
(58) Field of Search .................................. 606/159, 170; 604/95; 600/585; 408/199; 433/165, 166

(56) References Cited

U.S. PATENT DOCUMENTS 4,244,362 A * 1/1981 Anderson .............. 128/200.26
4,895,560 A * 1/1990 Papantonakos ............... 604/22
5,649,941 A * 7/1997 Lary .......................... 606/159
5,667,490 A * 9/1997 Keith et al. ................... 604/22
5,845,646 A * 12/1998 Lemelson .................... 128/899

* cited by examiner

Primary Examiner—Samuel G. Gilbert
(74) Attorney, Agent, or Firm—Harness, Dickey & Pierce, P.L.C.

(57) ABSTRACT

A magnetically navigable atherectomy device includes a cutting head, a flexible drive shaft having a proximal and a distal end, with the cutting device on the distal end, and a magnet associated with the cutting head, the magnet of sufficient size to allow the cutting head to be oriented by an externally applied magnetic field. The magnet may be a portion of the cutting head made from a magnetically permeable or permanent magnetic material, a portion of the drive shaft made from a magnetically permeable or permanent magnetic material; a separate magnet between the cutting head and the drive shaft, a portion a magnet on a sheath covering the drive shaft. Alternatively a guide wire can provided with a magnetic material on its distal end. Through the application of a magnetic field and/or a magnetic gradient, the artherectomy device can be guided to the location of the atheromatous material in the body. Once at the site of atheromatous material, through the application of a magnetic field or magnetic gradient, the device can be manipulated into proximity to the atheromatous material to remove the material.

2 Claims, 3 Drawing Sheets

MAGNETICALLY NAVIGABLE AND/OR CONTROLLABLE DEVICE FOR REMOVING MATERIAL FROM BODY LUMENS AND CAVITIES

This is a continuation patent application of U.S. patent application Ser. No. 09/281,241, filed Mar. 30, 1999, now U.S. Pat. No. 6,428,551, issued Aug. 6, 2002, which is a continuation in part of U.S. patent application Ser. No. 09/165,694, filed Oct. 2, 1998 now ABN.

FIELD OF THE INVENTION

This invention relates to devices for removing material from body lumens and cavities, and in particular to such devices that can be magnetically navigated and/or controlled.

BACKGROUND OF THE INVENTION

There are many medical conditions where it is desirable to remove material from the surface of a body lumen or cavity. For example in the case of occluded blood vessels, one method of treating this condition to use a cutting tool in the blood vessel to remove accumulated atheromatous material. These tools, frequently called atherectomy devices, typically comprise a blade or cutting bit or burr on the distal end of a flexible drive shaft. The drive shaft is preferably contained within a flexible sheath to protect the walls of the blood vessels from the rotation of the drive shaft. Examples of such devices include Shiber, U.S. Pat. No. 4,842,579, Simpson et al., U.S. Pat. No. 5,047,040; and Auth et al., U.S. Pat. No. 5,314,407, incorporated herein by reference.

An atherectomy device is typically navigated to the site of the disease by mechanically manipulating a guide wire to the site of the disease, and then advancing the atherectomy device over the guide wire to the site. The navigation of the guide wire through the blood vessel can be a slow and tedious process, requiring great skill. Once at the site of the disease, it can be difficult to precisely control the atherectomy device to satisfactorily remove the atheromatous material. Part of this difficulty arises from guide wire bias, for example as the atherectomy device traverses bends in the blood vessels the guide wire and device tend to move toward the outside of the bend, making it difficult to remove atheromatous material from the insides of the bends. Even in straighter segments of blood vessels, it is difficult to control the position of the atherectomy device within the cross section of the blood vessel, or the orientation of the cutting head of the atherectomy device within the blood vessel, and thus it is difficult to form a passage through the vessel larger than that cross section of the tool.

SUMMARY OF THE INVENTION

The present invention relates to an atherectomy device that can be magnetically controlled, and to the magnetic control of atherectomy devices. Generally, the atherectomy device of the present invention comprises a flexible drive shaft, with a cutting head on the distal end of the drive shaft. A magnet is associated with the cutting head. In one construction, the cutting head itself is made of a magnetic material, either a permanent magnet or a permeable magnet. In another construction a magnet is disposed between the cutting head and the drive shaft. In still another construction, the distal end portion of the drive shaft adjacent the cutting head is magnetic. In still another construction, a magnet is positioned on the distal end of the sheath, in proximity to the cutting head. The magnet can be any material with magnetic properties (i.e., responsive to a magnetic field or magnetic gradient), and may either be a separate part or constitute a magnetic portion of an existing part.

The magnet associated with the cutting head facilitates navigation of the atherectomy device to the procedure site, and control of the cutting head at the procedure site through the application of a magnetic field and/or magnetic field gradient. A magnetic field can be applied to orient the atherectomy device in the blood vessel for navigating to the procedure site. The applied magnetic field aligns the magnet associated with cutting head in the direction of the field, so that the atherectomy device can be more easily steered through the blood vessels. The device can then be advanced in the desired direction simply by pushing on the proximal end. Alternatively, or in addition, a magnetic field gradient can be applied to the magnet associated with the cutting head to apply force to the atherectomy device to actually move the device through the blood vessel, or assist the mechanical pushing of the device through the blood vessel. Once at the procedure site, magnetic fields and/or magnetic field gradients can be applied to the magnet associated with the cutting head to control the orientation of the device and its position within the cross-section of the blood vessel. Thus, with the application of a magnetic field, the cutting portion of the cutting head can be oriented toward the accumulated atheromatous material, and the cutting tool itself can be moved within the cross-section of the blood vessel to act on the accumulated atheromatous material, for example on the insides of bends. Because the tool can be both oriented and moved, the tool can open a passage in the blood vessel that is larger than the cross section of the device itself. By automating the control of the direction and/or gradient of the applied magnetic field, the procedure can be automated, so that once the tool is navigated to the site of the disease, the tool is automatically precessed to clear the cross-section of the vessel in adjacent the atherectomy device of the atheromatous material. In addition to precessing the cutting head by continuously changing the magnetic field, it is also possible to continuously move the cutting head around the cross-section of the vessel by continuously varying the magnetic gradient. Of course both the magnetic field and magnetic gradient can be simultaneously changed to cause the orientation and the position of the cutting head to change to remove material from around the cross section of the vessel.

In accordance with another embodiment of this invention, it is also possible that instead of, or in addition to, associating a magnet with the cutting head, the atherectomy device can be used in conjunction with a magnetic guide wire. A magnet can be provided on the end of a conventional guide wire, or a portion of the guide wire can be made magnetic. The guide wire is then navigated to the diseased site. The magnet on or in the guide wire facilitates orienting and /or moving the guide wire through the blood vessels. Once at the site, the atherectomy device can be brought into close association with the magnet on the guide wire, and the magnet on the guide wire can be used to orient and to move the cutting head within the blood vessel.

The atherectomy device of the present invention can be quickly and easily navigated to the site of the disease. This makes the procedure easier on the physician and the on patient. Once at the site, the tool can be operated more effectively, removing atheramotous material from around the entire circumference of the blood vessel, and clearing a passageway larger than the cross section of the atherectomy device itself. These and other features and advantages will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE INVENTION

Figure 1:
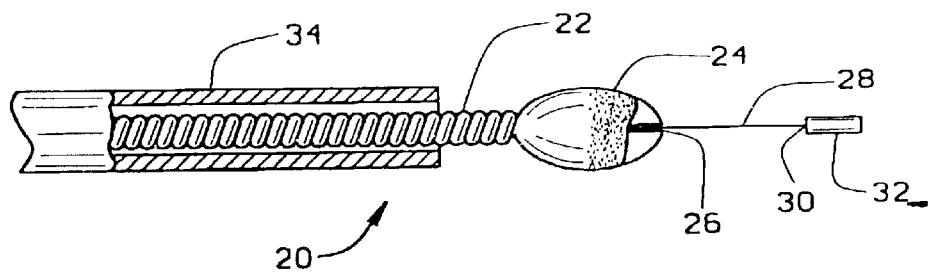
FIG. 1 is a partial longitudinal cross sectional view of an atherectomy device constructed according the principles of this invention.

An atherectomy device constructed according to the principles of this invention is indicated generally as 20 in FIG. 1. While the drawings and description of this preferred embodiment show and describe an atherectomy device for removing atheromatous material from the walls of blood vessels, the invention is not so limited, and applies to any magnetically navigable and/or controllable device for removing material from the surface of a body lumen or cavity. As shown in FIG. 1, the atherectomy device 20 comprises a flexible drive shaft 22 and a cutting head 24. The drive shaft 22 is preferably made from a tight helically coiled wire. The cutting head 24 is preferably an oblate spheroid, with an abrasive, such as diamond particles on the distal end. The drive shaft 22 rotates the cutting head 24, and the abrasive on the distal end of the cutting head abrades the atheromatous material in the vessel. There is a passage 26 through cutting head 24, and through the drive shaft 22 for receiving a guide wire 28. The guide wire 28 can be advanced in the blood vessel and then the atherectomy device 20 is advanced over the guide wire to the procedure site. The end 30 of the guide wire 28 may have a stop 32, to prevent the guide wire from being withdrawn entirely into the passage 26, and to blunt the end of the guide wire so that it does not puncture the blood vessel. Of course, as described below, the athrectomy device can be used without a guide wire and guided magnetically. This is particularly advantageous in totally occluded vessels where the guide wire cannot extend in front of the atherectomy device because of the occlusion. According to the principles of this invention, the cutting head 24 is made from or contains a magnetic material, for example a permanent magnetic materials such as Hiperco® (available from Carpenter Steel, Reading, Pa.) or a permeable magnetic material such as neodymium-iron-boron (Nd—Fe—B) (available from Magstar Technologies, Minneapolis, Minn. The cutting head 24 may be coated with an abrasive material, such as diamond dust embedded in the distal surface of the head.

The drive shaft 22 is preferably enclosed in a sheath 34, that protects the blood vessel from the rotating drive shaft. The sheath 34 may be made of a conventional medical catheter material such as polyvinylchloride.

Figure 2:
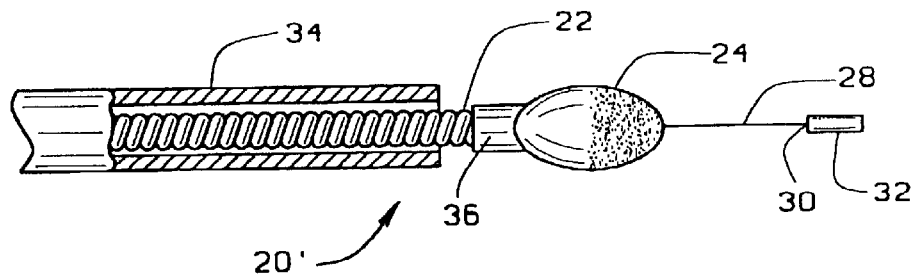
FIG. 2 is a partial longitudinal cross sectional view of an alternate construction of the atherectomy device, incorporating a discrete magnet.

A first alternative construction of the atherectomy device 20, indicated as 20', is shown in FIG. 2. The atherectomy device 20' is similar in construction to atherectomy device 20, except that instead of the cutting head 24 being made from a magnetic material, a magnet 36 is disposed between the drive shaft 22 and the cutting head 24. This magnet may be a permanent magnetic material such as Hiperco®, or a permeable magnetic material such as Nd—Fe—B.

Figure 3:
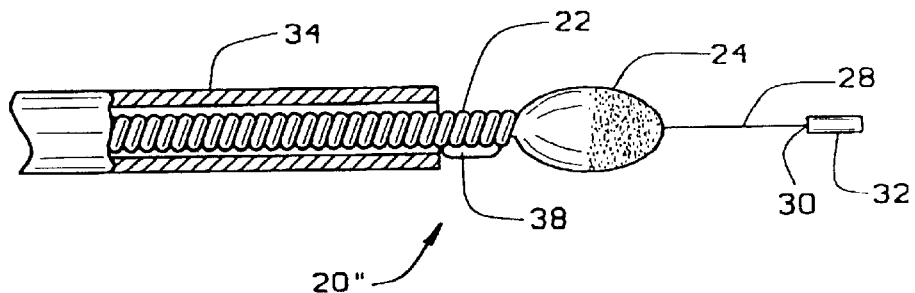
FIG. 3 is a partial longitudinal cross-sectional view of an alternate construction of the atherectomy device, in which a portion of the drive shaft is magnetic.

A second alternative construction of the atherectomy device 20, indicated generally as 20", is shown in FIG. 3. The atherectomy device 20" is similar in construction to atherectomy device 20, except that instead of the cutting head 24 being made from a magnetic material, the distal portion 38 of drive shaft 22 is magnetic. This distal portion may be made from a permanent magnetic material such as Hiperco® or a permeable magnetic material such as Nd—Fe—B.

Figure 4:
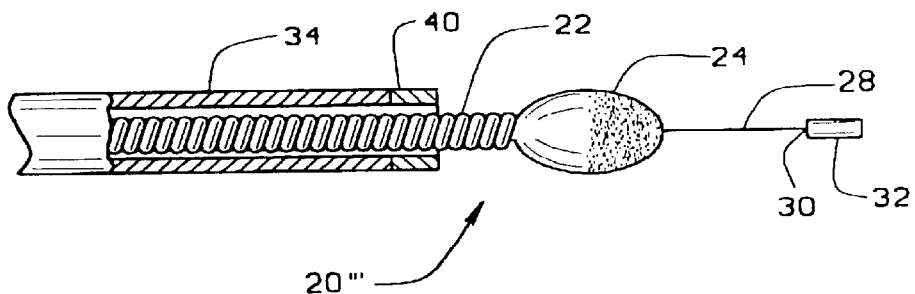
FIG. 4 is a partial longitudinal cross-sectional view of an alternate construction of the atherectomy device, incorporating a magnet on the sheath.

A third alternative construction of the atherectomy device 20, indicated generally as 20'" is shown in FIG. 4. The atherectomy device is similar in construction to atherectomy device 20, except that instead of the cutting head 24 being made from a magnetic material, the distal portion of the sheath has a magnet 40 thereon. The magnet may be embedded in the distal end portion of the catheter, or secured on the end, for example with a suitable medical grade adhesive. The cutting head can be retracted against the magnet 40, so that the magnet is closely associated with the cutting head 24.

Regardless of the means by which the magnet is associated with the atherectomy device, a magnetic field can be applied to orient the atherectomy device in the blood vessel for navigating to the procedure site. The externally applied magnetic field may be applied, for example with a magnetic surgery system like that disclosed in co-pending U.S. patent application Ser. No. 08-920,446, filed Aug. 29, 1997, entitled Method and Apparatus for Magnetically Controlling Motion Direction of a Mechanically Pushed Catheter, incorporated herein by reference. The applied magnetic field aligns the magnet associated with cutting head, e.g., the magnetic cutting head 24 in device 20, the magnet 36 associated with the cutting head in device 20', or the magnetic distal end portion 38 of the drive shaft 22 in device 20", in the direction of the field, so that the atherectomy device can be more easily steered through the blood vessels. Once the distal end of the device is oriented in the desired direction of travel by the magnetic field, the device can then be advanced in the desired direction simply by pushing on the proximal end. Alternatively, or in addition, a magnetic field gradient can be applied to the to the magnet associated with the cutting head to apply force to the atherectomy device to actually advance the device through the blood vessel. This force can be the only force used to move the atherectomy device, or this force can merely be used to assist the mechanical pushing of the device through the blood vessel.

Figure 5A:
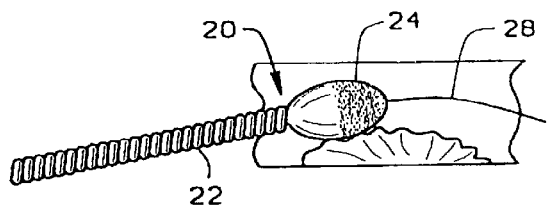
FIG. 5A is a longitudinal cross-sectional view of a blood vessel showing an atherectomy device of the present invention therein before the application of a magnetic gradient.
Figure 5B:
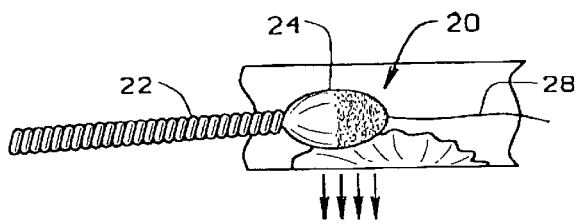
FIG. 5B is a longitudinal cross-sectional view of a blood vessel showing an atherectomy device of the present invention therein during the application of a magnetic gradient.
Figure 6A:
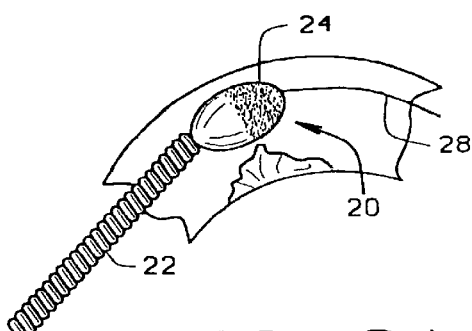
FIG. 6A is a longitudinal cross-sectional view of a curved segment of a blood vessel showing an atherectomy device of the present invention therein, before the application of a magnetic gradient.
Figure 6B:
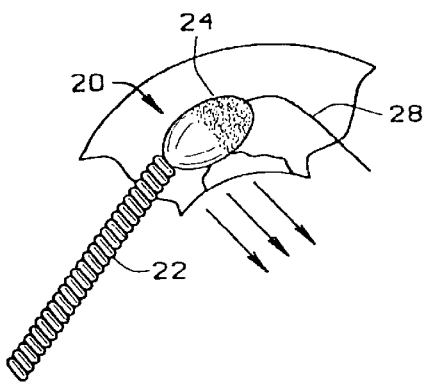
FIG. 6B is a longitudinal cross-sectional view of a curved segment of a blood vessel showing an atherectomy device of the present invention therein, during the application of a magnetic gradient.
Figure 7:
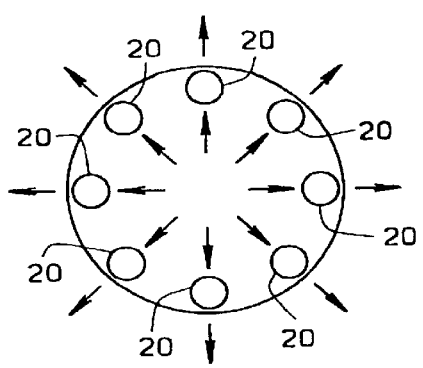
FIG. 7 is a transverse cross section of a blood vessel showing the possible positions of an atherectomy device of the present invention with the application of a magnetic gradient.

Once at the site, magnetic fields can be applied to the magnet associated with the cutting head to control the orientation of the device and its position within the cross-section of the blood vessel. Thus, with the application of a magnetic field, the cutting portion of the cutting head can be oriented toward the accumulated atheromatous material, and the cutting tool itself can be moved within the cross-section of the blood vessel to act on the accumulated atheromatous material, for example on the insides of bends. FIG. 5A shows an atherectomy device 20 in a blood vessel. The device is positioned generally along the guide wire 28. However, as shown in FIG. 5B upon the application of a magnetic field gradient, the cutting head 24 can be drawn toward the accumulated atheromatous material, to more completely and effectively abrade the material from the vessel wall. This technique is particularly advantageous in the bends of blood vessels, as shown in FIG. 6A, wherein the natural stiffness of the guide wire and the device causes the atherectomy device to a position away from the inside of the curve and toward the outside of the curve. However, as shown in FIG. 6B, upon the application of a magnetic field gradient, the cutting head 24 can be drawn against the accumulated atheromatous a material on the inside of the bend, to remove this material and more completely open the blood vessel. As shown in FIG. 7, by controlling the direction of the applied magnetic gradient, it is possible to move the cutting head to any position in the cross section of the blood vessel.

Figure 8:
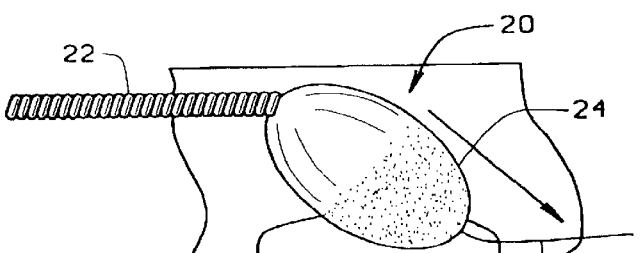
FIG. 8 is a longitudinal cross-sectional view of the blood vessel showing a atherectomy tool oriented by a magnetic field to remove accumulated atheromatous material.

As shown in FIG. 8, it is also possible to apply a magnetic field to simply orient the cutting head 24, positioning the distal abrasive cutting surface of the cutting head against the atheromatous material on the vessel wall. The effects of orientation with a magnetic field and positioning with a magnetic gradient can be combined. While the gradient pulls the cutting head into the atheromatous material, the field direction can be along the axis of the vessel, to keep the cutting head oriented along the vessel. Alternatively, the field direction can be at an angle with respect to the vessel, to tilt the cutting head into the atheromatous material.

Further, by continuously moving the applied magnetic field, it is possible to precess the cutting head 24 around the circumference of the vessel, moving the cutting head to clear substantially the entire cross section of the vessel. By employing a microprocessor control, or other automated control to change the magnetic field as a function of time, the cutting tool can be automatically precessed within the vessel. Thus the atherectomy tool can be used to create a flow pathway through the vessel that is actually larger than the cross section of the atherectomy device. As the cutting head is precessing, it can be slowly advanced across the accumulated atheromatous material. In addition to precessing the cutting head by continuously changing the magnetic field, it is also possible to continuously move the cutting head around the cross-section of the vessel by continuously varying the magnetic gradient. Of course both the magnetic field and magnetic gradient can be simultaneously changed to cause the orientation and the position of the cutting head to change to remove material from around the cross section of the vessel.

Figure 9A:
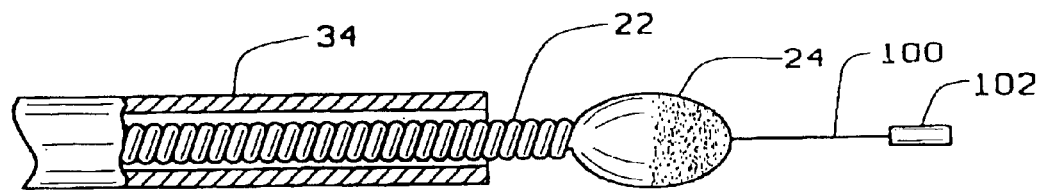
FIG. 9A is a partial longitudinal cross sectional view of an atherectomy device constructed according to the principles of this invention, employing a magnetic guide wire with a discrete magnet.
Figure 9B:
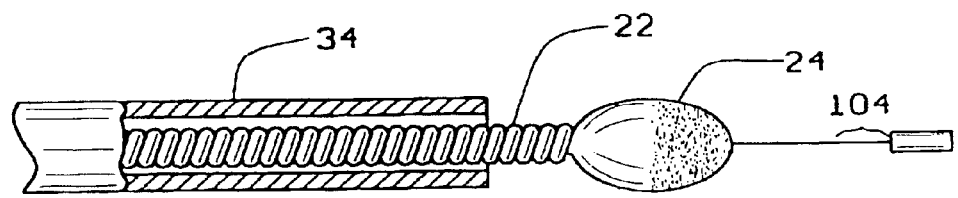
FIG. 9B is a partial longitudinal cross sectional view of an atherectomy device constructed according to the principles of this invention, employing a magnetic guide wire with a magnetic portion.

In accordance with a second embodiment of this invention, shown in FIGS. 9A and 9B, it is also possible that instead of, or in addition to, associating a magnetic with the cutting head, the atherectomy device can be used in conjunction with a magnetic guide wire 100, having a magnetic distal end portion. As shown in FIG. 9A, the guide wire 100 has a discrete magnet 102 on its distal end. As shown in FIG. 9B, the distal end portion 104 of the guide wire 100 is made from a magnetic wire material. The guide wire is then navigated to the diseased site. The magnet on or in the guide wire facilitate orienting and/or moving the guide wire through the blood vessels. Once at the site, the atherectomy device can be brought into close association with the magnet on the guide wire, and the magnet on the guide wire can be used to orient and to move the cutting head within the blood vessel.

Figure 10:
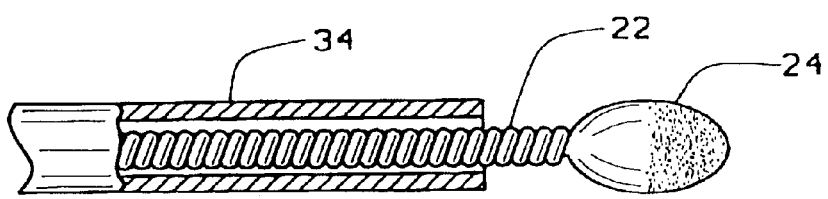
FIG. 10 is a partial longitudinal cross sectional view of an athrectomy device constructed according to the principles of this invention without a guide wire.

In accordance with a third embodiment of this invention, shown in FIG. 10, the atherectomy device can be used without any guide wire. The device is navigated solely by the application of magnetic fields and/or gradients, which apply a force through the magnet associated with the cutting head. One method of navigating such an atherectomy device is that disclosed in co-assigned U.S. patent application Ser. No. 60/095,710 filed Aug. 7, 1998, and incorporated herein by reference. In this method of navigation, the operating region in the patient is viewed on two planar fluoroscopic images of the operating region. The physician identifies the current position of the atherectomy device on each display, for example by using a mouse or similar device to point and click on the desired location. Similarly the physician can identify the desired new position of the atherectomy device on each display. A computer can control an electromagnetic system for generating an electromagnetic field and/or gradient for orienting and/or moving the distal end of the atherectomy device as input by the physician. The distal end of the atherectomy device is advanced manually or automatically, or in some cases it can be moved by a magnetic field or gradient. In this manner, the atherectomy device can be magnetically directed to the site of the occlusion without a guide wire, and once at the site of the occlusion can be magnetically manipulated to remove the material blocking the vessel or lumen.

What is claimed:

1. A device for removing material from the surface of body lumens and cavities, the device comprising:
   a cutting head;
   a drive shaft for driving the cutting head;
   a sheath, over the drive shaft; and
   a magnet on the distal end of the sheath, the magnet of sufficient size to allow the cutting head to be oriented by an externally applied magnetic field.

2. The device according to claim 1 further comprises a generally axially extending passage through the cutting head and the drive shaft for accommodating a guide wire.

* * * * *